United States Patent [19]

Wang et al.

[11] Patent Number: 4,713,069
[45] Date of Patent: Dec. 15, 1987

[54] BAFFLE HAVING ZONED WATER VAPOR PERMEABILITY

[75] Inventors: Kenneth Y. Wang, Roswell; Richard S. Yeo, Dunwoody, both of Ga.

[73] Assignee: Kimberly-Clark Corporation, Neenah, Wis.

[21] Appl. No.: 925,446

[22] Filed: Oct. 31, 1986

[51] Int. Cl.$^4$ .............................................. A61F 13/16
[52] U.S. Cl. .................................... 604/378; 55/158; 604/382
[58] Field of Search .................... 55/16, 158; 604/358, 604/359, 378, 380, 381, 382, 383, 384; 128/155-156

[56] References Cited

U.S. PATENT DOCUMENTS

| | | | |
|---|---|---|---|
| 3,016,599 | 1/1962 | Perry, Jr. | |
| 3,156,242 | 11/1964 | Crowe | 128/96 |
| 3,203,419 | 1/1963 | Joa | |
| 3,250,080 | 5/1966 | Garwin | 55/16 |
| 3,253,715 | 5/1966 | Painter et al. | 210/504 |
| 3,335,545 | 8/1967 | Robb et al. | 55/158 |
| 3,369,343 | 2/1986 | Robb | 55/158 |
| 3,426,754 | 2/1969 | Bierenbaum et al. | 128/156 |
| 3,518,041 | 6/1970 | Brelich | 8/115.7 |
| 3,590,585 | 7/1971 | DeWinter | 405/24 |
| 3,597,307 | 8/1971 | Paulusma et al. | 428/142 |
| 3,612,054 | 10/1971 | Matsuda et al. | |
| 3,640,829 | 2/1972 | Elton | 428/315.7 |
| 3,679,538 | 7/1972 | Druin et al. | |
| 3,704,198 | 11/1972 | Prentice | |

(List continued on next page.)

FOREIGN PATENT DOCUMENTS

| | | |
|---|---|---|
| 0105629 | 4/1984 | European Pat. Off. |
| 0141592 | 5/1985 | European Pat. Off. |
| 0184392 | 11/1986 | European Pat. Off. |
| 3417909 | 11/1985 | Fed. Rep. of Germany |
| 57-142323 | 9/1982 | Japan |
| 2103537 | 2/1983 | United Kingdom |
| 2115702 | 10/1985 | United Kingdom |

OTHER PUBLICATIONS

Mono-Sol 1-000 Series Hot Water Soluble Plastic Film data sheet, (Mono-Sol Division, Chris Craft Industries, Inc. Gary, Indiana 46403).

"Resins, Water-Soluble," a chapter from Kirk-Othmer Encyclopedia of Chemical Technology, Third Edition, vol. 20, John Wiley and Sons, New York, 1982, pp. 207-230.

"Vinyl Polymers (Poly(Vinyl Alcohol))," a chapter in Kirk-Othmer Encyclopedia of Chemical Technology, Third Edition, vol. 23, John Wiley and Sons, New York, 1983, pp. 848-865.

Vinol Poly(Vinyl Alcohol)) product line brochure, Air Products and Chemicals, Inc., Polymer Chemicals, Allentown, Pa. 18105.

(List continued on next page.)

Primary Examiner—C. Fred Rosenbaum
Assistant Examiner—Denise Whelton
Attorney, Agent, or Firm—William E. Maycock

[57] ABSTRACT

A baffle having a central zone extending along at least a portion of its length, A. the central zone being impermeable to menses under a static pressure of from about 1 to about 3 psi for a period of at least about one hour and having a water vapor transmission rate at 37 degrees C. and about 50 percent relative humidity of from about 50 to about 2,5000 g/m$^2$/24 hours, B. with the non-central zone portions of the baffle being impermeable to menses under a dead weight pressure of from about 0.1 to about 1 psi for a period of at least about one hour and having a water vapor transmission rate at 37 degrees C. and about 50 percent relative humidity of from about 1,500 to about 5,000 g/m$^2$/24/ hours;

with the proviso that the water vapor transmission rate of the central zone is less than that of the non-central zone portions of the baffle.

In preferred embodiments, the baffle is constructed from a nonwoven web, such as a meltblown web, or a laminate of two or more layers of nonwoven webs, such as a spunbonded-meltblown laminate, and the central zone includes an additional layer which is a continuous film of a poly(vinyl alcohol).

44 Claims, 2 Drawing Figures

U.S. PATENT DOCUMENTS

| | | | |
|---|---|---|---|
| 3,755,527 | 8/1973 | Keller et al. | |
| 3,843,761 | 10/1984 | Bierenbaum et al. | |
| 3,849,241 | 11/1974 | Butin et al. | |
| 3,869,310 | 3/1975 | Fukushima et al. | 427/333 |
| 3,870,593 | 3/1975 | Elton et al. | 128/156 |
| 3,891,487 | 6/1975 | Hoey | 156/78 |
| 3,932,682 | 1/1976 | Loft et al. | 428/296 |
| 4,006,052 | 2/1977 | Wang | 156/280 |
| 4,100,324 | 7/1978 | Anderson et al. | |
| 4,178,271 | 12/1979 | Busch et al. | 524/30 |
| 4,181,127 | 1/1980 | Linsky et al. | 128/155 |
| 4,197,148 | 4/1980 | Shinomura | |
| 4,197,371 | 4/1980 | Holst et al. | 521/84.1 |
| 4,226,906 | 10/1980 | Jacob | 428/283 |
| 4,247,498 | 1/1981 | Castro | 264/41 |
| 4,257,997 | 3/1981 | Soehngen et al. | |
| 4,289,832 | 9/1981 | Schwarz | |
| 4,304,812 | 12/1981 | Perkins | 428/247 |
| 4,308,303 | 12/1981 | Mastroianni et al. | 428/90 |
| 4,347,844 | 9/1982 | Ohki et al. | 604/368 |
| 4,384,023 | 5/1983 | Okamura et al. | |
| 4,415,617 | 11/1983 | D'Elia | 428/86 |
| 4,430,278 | 2/1984 | Jones, Sr. | |
| 4,452,845 | 6/1984 | Lloyd et al. | |
| 4,454,191 | 6/1984 | vonBlucher et al. | 428/244 |
| 4,472,328 | 9/1984 | Sugimoto et al. | |
| 4,485,809 | 12/1984 | Dellas | 128/156 |
| 4,516,571 | 5/1985 | Buchan | 128/132 R |
| 4,519,909 | 5/1985 | Castro | 210/500.27 |
| 4,539,256 | 9/1985 | Shipman | |
| 4,560,611 | 12/1985 | Naka et al. | 428/266 |
| 4,561,435 | 12/1985 | McKnight et al. | 128/156 |
| 4,578,069 | 3/1986 | Whitehead et al. | |
| 4,591,523 | 5/1986 | Thompson | 428/131 |
| 4,595,001 | 6/1986 | Potter et al. | |
| 4,603,077 | 7/1986 | Fujimoto et al. | |
| 4,608,111 | 8/1986 | Hume, III et al. | |

OTHER PUBLICATIONS

Vinol Poly(Vinyl Alcohol) product bulletin, Air Products and Chemicals, Inc., Polymer Chemicals, Allentown, PA 18105.

BAFFLE HAVING ZONED WATER VAPOR PERMEABILITY

CROSS-REFERENCES TO RELATED APPLICATIONS

A breathable barrier which comprises a porous sheet coated with poly(vinyl alcohol) or laminated to a poly(vinyl alcohol) film is described and claimed in copending and commonly assigned application Ser. No. 926,033, entitled BREATHABLE BARRIER, filed of even date in the names of Richard S. Yeo and Daniel K. Schiffer. The use of a continuous film of a poly(vinyl alcohol) joined to a porous substrate having a controlled structure is described and claimed in copending and commonly assigned application Ser. No. 925,425, entitled BREATHABLE CLOTHLIKE BARRIER HAVING CONTROLLED STRUCTURE DEFENSIVE COMPOSITE, filed of even date in the names of Kenneth Y. Wang and Richard S. Yeo. Finally, a barrier having at least three layers, one of which is a continuous film of a poly(vinyl alcohol), is described and claimed in copending and commonly assigned application Ser. No. 925,332, entitled BREATHABLE, MULTILAYERED, CLOTHLIKE BARRIER, filed of even date in the names of Ralph V. Braun, Lance Garrett, Robert J. Phelan and Richard S. Yeo.

BACKGROUND OF THE INVENTION

The present invention relates to a baffle suitable for use in a feminine pad or napkin. More particularly, the present invention relates to a baffle having zoned water vapor permeability.

In a feminine pad, there obviously is a requirement for protection against leakage of body fluids through the pad. The component of the pad offering such protection is referred to in the art as a baffle. Such requirement for protection against leakage is most critical in a target area generally confined to an approximately 7.6-cm by 3.8-cm zone in the center of the pad. On the other hand, however, the pad should be breathable, i.e., pervious to water vapor, in order to provide maximum comfort for the wearer.

Past attempts to provide pads meeting both requirements appear to have used either of two approaches. In the first approach, the baffle completely covers the exterior of the pad which is located away from the body and is impervious to menses while being permeable to water vapor. An example of such a baffle is given in U.K. Patent No. GB 2,115,702B. The patent is directed toward an absorbent article, such as a disposable diaper or sanitary napkin, in which the article has a vapor-permeable, liquid-impermeable backing sheet. The backing sheet is composed of a film produced by mixing 100 parts by weight of a polyolefin resin, 28 to 200 parts by weight of a filler, and 10 to 70 parts by weight of a liquid or wax-like hydrocarbon polymer, molding the mixture to form a film, and then stretching the film laterally and/or longitudinally until it has a dimension of more than 1.2 times its original dimension in that direction, thereby resulting in the formation of fine pores in the film. Examples of polyolefins include polyethylene and polypropylene. A variety of fillers can be used, and examples of the hydrocarbon polymer include polybutadienes, liquid polybutenes, and hydrogenates of liquid polybutadienes, among which saturated polyhydroxy-substituted hydrocarbons obtained by hydrogenating hydroxy-terminated liquid polybutadienes are preferred. See also U.S. Pat. No. 3,870,593 which describes stretching a film containing finely divided particles of a nonhygroscopic inorganic salt, such as calcium carbonate, in order to obtain a microporous film. The microporous sheet material described in U.S. Pat. No. 3,640,829 also involves incorporating within the polymer an inorganic salt which is leached out to produce the micropores.

The second approach involves the use of a liquid repellent sheet on the outermost side of the absorbent layers. In U.S. Pat. No. 3,203,419, such sheet has a surface area smaller than that of the absorbent layer against which it is placed. In U.S. Pat. No. 3,612,054, the absorbent layers have placed within them at least one barrier sheet of a liquid repellent material which has a surface area smaller than that of the absorbent layers.

In general, various breathable outer covers, baffles, or other materials are known. In the context of such materials, the term "breathable" has reference only to the ability of water vapor to pass through the material and is used throughout this specification in the same way.

By way of illustration, U.S. Pat. No. 3,156,242 discloses a flexible absorbent sheet which is useful as a surgical dressing. The backing sheet or outer layer of the dressing is either air pervious by nature, such as a microporous film, or has had holes or slits formed in it. The example employed a perforated polyethylene film.

U.S. Pat. No. 3,426,754 teaches a breathable medical dressing. Such dressing comprises a backing having an open-celled structure, preferably coated with a continuous layer of a microporous pressure-sensitive adhesive. The backing employs a plastic film to which the desired properties have been imparted as a result of special processing conditions. The film typically can be prepared from polyolefins, polyacetals, polymethylene sulfide, polyethylene sulfide, polyphenylene oxide, polyamides, polyesters, and the like. The film possesses an open-celled structure, the voids of which are accessible to the outside surface by means of passageways which generally are under 5,000 Angstroms, e.g., from 100 to 5,000 Angstroms. In addition, such film has a final crystallinity of at least 40 percent.

A porous sheet and a process for making it are described in U.S. Pat. No. 4,347,844. The sheet is reported to be useful as a water-impermeable, vapor-permeable backing sheet for disposable diapers. The sheet contains a filler, the particles of which have been broken by the application of a compressive force to cause the formation of voids or spaces, i.e., micropores, which permit the passage of water vapor through the sheet while acting as a barrier to liquid water. The sheet apparently can be made of a nonfoamed thermoplastic resin, such as polyethylene and nylon. In addition, the patent suggests that the film can be a composite of a polyethylene or nylon film and spunbonded polyethylene or polyester. The use of a spunbonded material alone does not appear to be within the scope of the disclosure.

U.S. Pat. No. 4,591,523 relates to an apertured, macroscopically expanded, three-dimensional polymeric web exhibiting breathability and resistance to fluid transmission. The web is reported to have particular utility as a breathable barrier for a disposable diaper. The web preferably comprises a deeply drawn three-dimensional structure containing a multiplicity of debossments of macroscopic cross-section (i.e., visibly perceivable by the normal human eye at a perpendicular distance of about one foot), each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. These smaller apertures in each end wall are so spaced relative to all adjacent apertures in the end wall that the aqueous fluid menisci supported in the apertures do not contact one another.

Waterproof products capable of transmitting air and water vapor which have fabric-like aesthetic properties are described in U.S. Pat. No. 3,932,682. The products are made by spray-spinning filamentary material directly onto an open-celled microporous polymer film, such that thermal self-bonding occurs between the filamentary material and the film, or by spray-spinning the filamentary material in the same manner onto an elastic film, stretching the resulting product until an open-celled structure is produced in the film portion of the product and thereafter heating or heat setting the resulting product at substantially constant length to impart dimensional stability thereto. Polymers suitable for making the film appear to be those described in U.S. Pat. No. 3,426,754, discussed hereinabove. As already noted, the filamentary material is produced by spray-spinning, i.e., meltblowing, directly onto the film.

U.S. Pat. No. 4,308,303 describes a flocked, foam coated, fibrous-reinforced, water vapor permeable barrier having the appearance of fabric and capable of filtering bacteria. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer. The film is rendered microporous by stretching a film which contains minute fracture sites or pore-nucleating agents such as finely divided filler and/or minute crystalline domains. The use of a finely divided, inorganic, water-insoluble, inert filler such as calcium carbonate having an average particle size of less than 3 microns is preferred.

U.S. Pat. No. 4,560,611 relates to a moisture permeable, waterproof coated fabric. Briefly, a microporous polyurethane layer is formed on a base fabric which may be knitted, woven, nonwoven, or the like. The coating solution consists of a polar organic solvent solution containing 8 to 25 percent by weight of a polyurethane elastomer, 0.1 to 10 percent by weight of a water repellent agent, 0.2 to 3 percent by weight of a polyisocyanate, and 1 to 8 percent by weight of a nonionic surfactant. The water repellent agent typically is a fluorine- or silicone-based material. The polyisocyanate usually will be any of the well known di- or triisocyanates. The polyurethane elastomer can be a polyester or polyether polyurethane.

A somewhat similar approach is described in European Patent Application No. 85308671.8, Publication No. 0 184 392 A2. A waterproof, moisture-vapor permeable unitary sheet material comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough, thereby rendering the sheet material breathable. Preferably, the average pore size will be less than about 10 percent of the thickness of the matrix. By way of example, the average pore size for a matrix having a thickness of about 10 to 50 micrometers typically will be on the order of 1 to 5 micrometers or less. By contrast, the average pore size or opening of a woven fabric is about the same magnitude as its thickness. A matrix having too large a pore size will permit the passage of water therethrough as hydrophilic material solidified therein will not sufficiently close the pores against the passage of liquid. The matrix can be prepared by known methods from any polymeric material which is substantially impenetrable by water. Suitable polymeric materials include polyolefins, polyesters, polyamides, and the like. The preferred hydrophilic material is polyethylene oxide which preferably is polymerized with a polyisocyanate to give a polyurethane.

U.S. Pat. No. 4,197,371 discloses a water vapor absorbing and transmitting sheet material. The sheet material comprises a natural or synthetic rubber or a rubber-like polymer having uniformly incorporated therein particles of at least one swellable modified polymer. Examples of suitable swellable modified polymers include, among others, modified starches and celluloses. Apparently, such sheet materials are not suitable for use as an outer covering for a disposable absorbent product, e.g., a diaper or sanitary napkin. See also U.S. Pat. No. 4,178,271 which describes a similar sheet material based on a sheet-like structure of poly(vinyl chloride) or a copolymer of vinyl chloride.

U.S. Pat. No. 3,869,310 describes flexible sheet materials which are leather-like. Although the materials allegedly have improved physical properties, particular properties, such as water vapor permeability, are not discussed. The materials comprise a nonwoven fibrous mat and a polymeric impregnant which has a porous structure and is substantially not bonded to the fibers of the mat. The materials are obtained by preparing a nonwoven fibrous mat composed of fibers prepared from at least two different polymeric materials, impregnating the mat with a first liquid which is a solvent for one of the polymeric materials and a nonsolvent for the other polymeric materials, dissolving the fibers composed of the polymeric material which is soluble in the liquid, and coagulating the polymer solution resulting from the addition of the first liquid into a porous polymeric structure which is substantially not bonded to the undissolved fibers by the addition of a second liquid which is a nonsolvent for all of the polymeric materials originally present in the nonwoven fibrous mat but which is at least partially miscible with the first liquid.

The list of suitable polymeric materials which can be employed includes poly(vinyl alcohol), although the preferred combinations of polymeric materials apparently are nylon-6 and polystyrene, nylon-6 and polypropylene, poly(ethylene terephthalate) and polystyrene, poly(vinyl chloride) and polypropylene, nylon-6 and poly(vinyl acetate), and nylon-6 and a polyurethane elastomer. One example, however, involved the use of a nonwoven mat composed of fibers of poly(vinyl chloride) and poly(vinyl alcohol); the first liquid was N,N-dimethylformamide which is a solvent for poly(vinyl alcohol) but a nonsolvent for poly(vinyl chloride).

The use of poly(vinyl alcohol) as a binder for a nonwoven fabric is described in U.S. Pat. No. 3,518,041.

The nonwoven fabric is composed of cellulose fibers alone or in combination with other natural or synthetic fibers. The binder is a poly(vinyl alcohol) resin in film, powder, fiber, or other particulate form which is crosslinked in situ with formaldehyde. The binder is applied to the fabric as an aqueous solution or poly(vinyl alcohol) fibers may be incorporated into the fabric and activated by treating the fabric with water. The fabric then is treated with an aqueous solution of formaldehyde which contains a catalyst.

A disclosure somewhat similar to that of the above patent is found in U.S. Pat. No. 3,253,715 which describes boil-proof nonwoven filter media. The media are prepared by treating a multilayered nonwoven fabric with a binder which is an aqueous solution of poly(vinyl alcohol) and a polyacrylic acid or crosslinked polyacrylic acid.

It is interesting to note that, in contrast to U.S. Pat. Nos. 3,518,041 and 3,253,715, U.S. Pat. No. 3,590,585 describes a composite structure, useful as an artificial seaweed, which employs water-decomposable poly(vinyl alcohol) filaments to temporarily hold buoyant, water-resistant strands in place during the handling, transporting, and installing of the product. Also of interest in this regard is U.S. Pat. No. 4,304,812 which describes the backcoating of an open-weave fabric. Prior to the backcoating step, a temporary protective coating is applied to the face of the fabric. After backcoating the fabric, the protective coating is removed with a solvent medium. Suitable protective coatings preferably are at least partially water soluble and include water-soluble poly(vinyl alcohol) or partially hydrolyzed poly(vinyl acetate).

U.S. Pat. No. 3,597,307 describes a supple sheet material which is composed of a fibrous nonwoven web and a polyurethane filler. The fibers of the web can be prepared from poly(vinyl alcohol) and the amount of the filler can be up to 30 percent by weight, based on the weight of the sheet material. Although the sheet material is stated to have a good water vapor pick-up value, it is not known if the material is permeable to water vapor. See also U.S. Pat. No. 4,006,052.

U.S. Pat. No. 3,891,487 discloses a decorative laminate which has a textile backing, a crushed thermoset plastic foam bonded thereto, and a transparent polymeric film overlaying the foam. The film preferably is cast from a latex; suitable materials for preparing the latex include poly(vinyl alcohol). The film can be made breathable by mechanically foaming the latex before casting, mechanically puncturing the film, using chemical blowing agents, or dissolving or digesting out temporary fillers placed in the latex before it is cast. The textile backing apparently can be either woven or nonwoven. The decorative laminate is useful as, for example, a simulated oil painting, and clearly is not intended to be contacted by water.

Microporous coated fabrics are described in U.S. Pat. No. 4,226,906. Microporosity apparently results from the use of clustered microspheres. The microspheres may be synthetic or naturally occurring. If the former, they are prepared by bonding individual microspheres in a matrix which is insoluble in the coating composition; the bonding agent for such matrix can be, for example, poly(vinyl alcohol). However, the patent does not appear to teach the use of poly(vinyl alcohol) in the preparation of microporous coated fabrics when naturally occurring microspheres are used; in such case, the coating composition was based on poly(vinyl chloride) and the fabric was a nonwoven polyester.

U.S. Pat. No. 4,415,617 discloses a base fabric for the manufacture of embroidery and lace. The base fabric is a nonwoven web of poly(vinyl alcohol) fibers which has been processed in such a manner as to convert one surface of the web into a gas-permeable film comprising thermoplasticized and rehardened, flattened fibers and portions of fibers. The base fabric then can be dissolved away from embroidery stitched thereon by exposing the fabric to water at a temperature of about 100 degrees C.

U.S. Pat. No. 4,454,191 describes a waterproof and moisture-conducting fabric coated with a hydrophilic polymer. The fabric can be a woven, knit, felt, or nonwoven material which is composed of natural, synthetic, or mineral fibers. The fabric itself must be permeable to water vapor. The fabric is sealed with a hydrophilic polymer which is capable of absorbing, transporting, and releasing water molecules. Such capability results from the presence in the polymer of hydrophilic groups, such as hydroxy, amino, ether, and carboxy groups. Thus, suitable polymers include those prepared from hydroxyalkyl acrylates, the acrylic or methacrylic esters of polyalkylene oxides or polyalkylenimides, and the like. Other suitable polymers include modified vinyl alcohol resins, regenerated cellulose, a poly(vinyl chloride) having built-in monomers which have powerful hydrophilic groups, copolymerizates of vinyl chloride and vinyl acetate in which the acetate groups have been hydrolyzed to hydroxy groups, and polyurethanes having excess hydroxy or amino groups.

A somewhat related disclosure is found in German Published Patent Application No. 3417909 A1, which describes the use of a water-soluble poly(vinyl alcohol) film in the resorbent material of a sanitary pad. The film reportedly prevents soiling of clothing while permitting sanitary disposal of the used article. There appears to be no mention of the characteristics of the film or where and how the film is placed in the pad.

It perhaps should be mentioned that there is a large body of literature on the preparation of microporous films, only a relatively small portion of which has been discussed hereinabove. While a detailed discussion of such body of literature is beyond the scope of this section, a limited number of additional, representative references perhaps should be mentioned for the sake of completeness. Such references include, by way of illustration only, U.S. Pat. Nos. 4,247,498, 4,519,909, 4,257,997, 4,452,845, 4,539,256, 3,843,761, 3,679,538, 4,430,278, 4,289,832, 4,384,023, 4,472,328, 4,197,148, U.K. Published Patent Application No. GB 2,103,537A, Japanese Published Patent Application No. 57-142323, and European Patent Application Nos. 84307198.6, Publication No. 0 141 592 A2, and 83305161.8, Publication No. 0 105 629 A2.

Finally, a more aesthetically pleasing barrier is described in U.S. Pat. No. 4,578,069. The barrier is a breathable baffle composite which is employed in the construction of a sanitary napkin. The baffle is formed by joining webs of a meltblown polyolefin and a spunbonded polyolefin, with the latter providing a surface for the adhesive which permits attachment of the napkin to an article of clothing.

Although various of the breathable barriers described above have proven useful in such absorbent articles as disposable diapers and sanitary napkins, there still is a need for an effective breathable outer cover or baffle which has a clothlike feel and can be manufactured cheaply in large quantities.

SUMMARY OF THE INVENTION

It therefore is an object of the present invention to provide a baffle suitable for use in a feminine pad or napkin.

Another object of the present invention is to provide a baffle having zoned water vapor permeability.

These and other objects will be readily apparent to one having ordinary skill in the art from a reading of the specification.

Accordingly, the present invention provides a baffle having a central zone extending along at least a portion of the length thereof, A. said zone being impermeable to menses under a static pressure of from about 1 to about 3 psi for a period of at least about one hour and having a water vapor transmission rate at 37 degrees C. and about 50 percent relative humidity of from about 50 to about 2,500 g/m$^2$/24 hours, B. with the non-central zone portions of the baffle being impermeable to menses under a static pressure of from about 0.1 to about 1 psi for a period of at least about one hour and having a water vapor transmission rate at 37 degrees C. and about 50 percent relative humidity of from about 1,500 to about 5,000 g/m$^2$/24 hours;

with the proviso that the water vapor transmission rate of the central zone is less than that of the non-central zone portions of the baffle.

In preferred embodiments, the central zone extends the entire length of the baffle. In other preferred embodiments, the central zone is at least about one-third the length of the baffle and centrally located lengthwise.

In still other preferred embodiments, the baffle comprises a clothlike porous substrate and the central zone comprises a menses impermeable, water vapor-permeable material overlaying and joined to the porous substrate. In other preferred embodiments, the menses impermeable, water vapor-permeable material is a continuous film of a water-soluble polymeric material.

In yet other preferred embodiments, the porous substrate is a fibrous porous substrate, such as a nonwoven web, and the menses impermeable, water vapor-permeable material is a continuous film of a water-soluble polymeric material, which film:

is not microporous in that it is substantially free of voids which connect the two surfaces of the film; and has an average thickness of from about 3 to about 250 microns.

In still other preferred embodiments, the side of the film overlaying and joined to said fibrous porous substrate is intimately comingled with at least some of the fibers of the continuous film side of said fibrous porous substrate and none of the pores at the surface of said fibrous porous substrate joined to said continuous film are so large as to significantly adversely affect the barrier properties of said baffle as a consequence of said comingling. In additional preferred embodiments, the water-soluble material is a poly(vinyl alcohol).

DETAILED DESCRIPTION OF THE INVENTION

Figure 1:
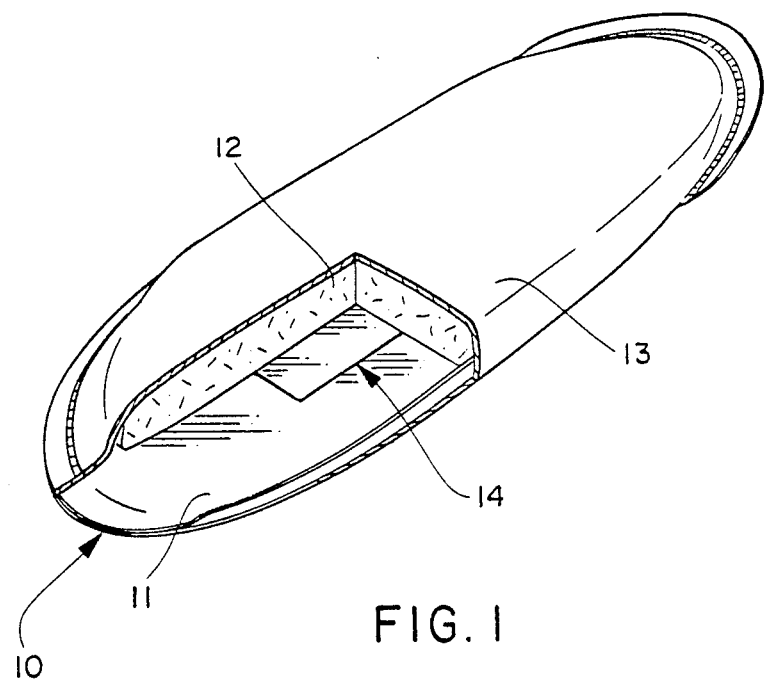
FIGS. 1 and 2 are perspective, cut away drawings illustrating two embodiments of the baffle of the present invention as incorporated into a sanitary pad.

As used herein, the term "zoned water vapor permeability" means that the water vapor permeability of a central area or zone of the baffle is less than that of the remaining baffle area. That is, the areas of the baffle on each side of the central zone will have a water vapor permeability greater than that of the central zone, whereas the areas of the baffle to the front and rear of the baffle may have a water vapor permeability equal to or greater than that of the central zone.

The term "menses impermeable, water vapor-permeable material" means that the material, in conjunction with the porous substrate to which it is joined, is permeable to water vapor and impermeable to menses under a static pressure of from about 2 to about 3 psi for a period of at least about one hour. For the purposes of the present invention, the material is permeable to water vapor if it and the porous substrate to which it is joined have a water vapor transmission rate at 37 degrees C. and about 50 percent relative humidity of from about 50 to about 2,500 g/m$^2$/24 hours.

The central zone represents that area of the baffle where the requirement for protection against leakage is the most critical. In general, the central zone is a centrally located area of the baffle which typically is at least about 7.6 cm long and about 3.8 cm wide. Thus, as a practical matter, the central zone should have a minimum area of approximately 29 cm$^2$. However, the dimensions of the central zone are not critical.

The areas of the baffle on each side of the central zone will be areas of higher water vapor permeability relative to that of the central zone. The areas of the baffle to the front and rear of the central zone can have a water vapor permeability which is equal to or greater than that of the central zone. Preferably, the central zone will extend the length of the baffle since by so doing the manufacturing process is made simpler.

The construction and materials selected for the zoned baffle of the present invention are not known to be critical, provided that the central zone has a water vapor permeability which is lower than that of the remainder of the baffle. However, either of two approaches typically will be employed: (1) the use of multiple layers and (2) a coating or its equivalent in the central zone. Baffles illustrative of these two approaches are the following:

(a) The baffle consists of a microporous film to which a meltblown web has been joined in the central zone.

(b) The baffle consists of a meltblown web or a spunbonded-meltblown laminate to which a second meltblown web has been joined in the central zone.

(c) The baffle consists of a microporous film or a meltblown web coated in the central zone with a wax, a fluorocarbon, or the like.

(d) The baffle consists of a meltblown web with a wax, fluorocarbon, or like material incorporated therein in a volume, the length and width of which correspond to the central zone.

(e) The baffle consists of a clothlike porous substrate and a water vapor-permeable material overlaying and joined to the substrate in the area of the central zone.

Of course, other constructions or combinations of materials will be apparent to those having ordinary skill in the art.

In general, illustrative baffle (e) is the preferred construction for a baffle of the present invention since it features low manufacturing costs, excellent barrier properties, and pleasing appearance and hand.

As already noted, then, the baffle of the present invention preferably will comprise a clothlike porous substrate and a water vapor-permeable material overlaying and joined to the substrate in the area of the central zone. In general, the clothlike porous substrate can be any clothlike porous material which is desired to be converted to a baffle. Thus, such porous substrate can be a paper substrate, i.e., a mat of cellulosic fibers, a woven web, a knitted fabric, a spunlaced material, a bonded carded web, a needle punched material, a nonwoven web, or the like. Preferably, however, the porous substrate will be a fibrous porous substrate, more preferably a nonwoven web. Most preferably, the porous substrate will be a spunbonded, meltblown, or coformed nonwoven web.

Various methods for making clothlike porous substrates are, of course, well known to those having ordinary skill in the art and need not be discussed herein. For the most preferred substrates, however, representative methods are described in, for example, U.S. Pat. Nos. 3,016,599, 3,755,527, 3,704,198, 3,849,241, 4,100,324, and 3,692,618, all of which are incorporated herein by reference. With respect to coformed webs, it perhaps should be noted that the web in general will consist of primary web-forming fibers with secondary fibers or particles dispersed therein.

The material from which the porous substrate is prepared is not known to be critical. When the porous substrate is a nonwoven web, the preferred materials for the preparation of the web are polyolefins. For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block copolymers of two or more polyolefins (or two or more different polyolefin monomeric precursors) or of one or more polyolefins and one or more nonpolyolefin polymers. Similarly, polymer blends can utilize two or more polyolefins or one or more polyolefins and one or more nonpolyolefin polymers. As a practical matter, homopolymers and copolymers and polymer blends involving only polyolefins are preferred, with homopolymers being most preferred.

Examples of polyolefins include polyethylene, polystyrene, poly(vinyl chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

By way of illustration, satisfactory baffles have been prepared using nonwoven webs, e.g., spunbonded or meltblown webs, with meltblown webs being preferred. With meltblown webs, nominal basis weights typically will be from about 15 to about 34 g/m$^2$. Moreover, as already suggested, the baffle can be a single layer or a composite of two or more layers.

As examples of multilayer constructions for the baffle, the baffle can be a laminate of a bonded carded web and a meltblown web. Alternatively, the baffle can be a laminate of a spunbonded web and a meltblown web. See, for example, U.S. Pat. No. 4,578,069, supra.

The menses impermeable, water vapor-permeable material generally can be any material meeting the requirements specified herein, numerous examples of which will be known to those having ordinary skill in the art. Perhaps the largest class of suitable materials will be microporous membranes or films.

Preferably, the menses impermeable, water vapor-permeable material is a continuous film of a water-soluble polymeric material. Such film can be a preformed film which is joined or laminated to the porous substrate or formed in situ from an aqueous coating on the porous substrate.

In general, the water-soluble polymeric material must be capable of forming or being formed as a continuous film which:

is not microporous in that it is substantially free of voids which connect the two surfaces of the film;

is capable of transporting water molecules through the thickness of the film as a result of the solubility of said water molecules in the polymeric material;

has an average thickness of from about 3 to about 250 microns; and has a water vapor transmission rate at 37 degrees C. and about 50 percent relative humidity of from about 100 to about 5,000 g/m$^2$/24 hours.

Such a film is not a microporous film as that term has been used in the art. That is, such film does not have voids or micropores which connect the two surfaces of the film. In a microporous film, the interconnecting voids provide a pathway for the transport of water molecules from one surface to another, the driving force being the differences in relative humidities at the two surfaces. As employed in the present invention, however, a film obtained from a water-soluble polymeric material as described herein utilizes a different mechanism, namely: water molecules must be soluble in the film and capable of being transported by means of such solubility from one surface of the film to the other.

In general, the water-soluble polymeric materials suitable for use in the present invention can be either natural or synthetic, and the former group of materials can be modified, if desired, to achieve particular properties. The natural and modified natural materials include, by way of illustration only, agar, carragenan, corn starch, guar gum, gum arabic, gum karaya, gum tragacanth, locust bean gum, potato starch, wheat starch, rice starch, tapioca, casein, gelatin, pectin, sodium alginate, xanthan gum, aminoalkyl starches, dextran, hydroxyalkyl starches, hydroxyethyl cellulose, hydroxypropyl cellulose, methyl cellulose, sodium carboxymethyl cellulose, and the like.

Examples of synthetic water-soluble polymeric resins include poly(vinyl alcohol), polyacrylamides, polyethyleneimine, Mannich-substituted polyacrylamides, poly(acrylic acid), poly(methacrylic acid), poly(dimethylaminoethyl methacrylate), polyalkylene polyamines, poly(vinylbenzyltrimethylammonium chloride), poly(diallyldimethylammonium chloride), poly(glycidyltrimethylammonium chloride), poly(ethylene oxide), poly(N-vinyl-2-pyrrolidinone), methyl vinyl ether-maleic anhydride copolymers and lower alkyl esters thereof, and the like.

In many cases, it may be necessary to include a cross-linking agent with the water-soluble polymeric material in order to obtain the requisite film properties. However, suitable crosslinking agents and their uses are well known to those having ordinary skill in the art.

When the continuous film is formed on the porous substrate in situ, the porosity of the porous surface, e.g., the sizes of the pores at the surface of the substrate on which the film will be formed, is of concern only in the sense that none of such pores can be so large as to interfere with the formation of the continuous film in a way which will significantly adversely affect the barrier properties of the baffle. It is important to note that perfection is not required; it is necessary only that those film imperfections which may be present do not result in a significant deterioration of baffle properties, particularly with respect to the passage of menses through the baffle.

In the case where the porous substrate is a meltblown web, one of the most preferred porous substrates, it is estimated that, in order to obtain generally satisfactory baffle properties, each of at least about 50 percent of the pores at the surface to be coated of the meltblown web should have a cross-sectional area of less than about $3.2 \times 10^{-8}$ m$^2$, with none of such pores being so large as to prevent the formation of the continuous film in such a manner as to significantly adversely affect the barrier properties of the baffle. Moreover, it is believed that optimum baffle properties should be possible with meltblown webs when essentially none of the pores at such surface has a cross-sectional area in excess of about $3.2 \times 10^{-8}$ m$^2$. Because of the numerous combinations of porous substrates and water-soluble polymeric materials which are possible, however, it is not feasible to do more than offer the foregoing guidelines with respect to the porosity of the porous substrate.

The use of synthetic water-soluble polymeric materials is preferred, with poly(vinyl alcohol) being most preferred. Because poly(vinyl alcohol) is most preferred it was used in the examples. The material and its use are described in greater detail below.

The continuous film of a poly(vinyl alcohol) will cover only the area of the central zone and must be joined to the porous substrate in order to prevent leakage of fluid from underneath the film. As already indicated, the film can be formed in situ from a coating of an aqueous solution of the poly(vinyl alcohol). Alternatively, a preformed poly(vinyl alcohol) film can be laminated to the porous substrate by known means. Because the formation of the film in situ is preferred, that procedure is emphasized in the comments which follow.

As is well known in the art, poly(vinyl alcohol) is a synthetic water-soluble polymeric material. There are, however, numerous grades of poly(vinyl alcohol), many of which have different solubility characteristics in water. For example, some grades are soluble in water at ambient temperature, while others are soluble in water only at elevated temperatures. At the present time, though, there are no known limitations with respect to the grade or nature of the poly(vinyl alcohol) employed in the preparation of the central zone.

Poly(vinyl alcohol), for convenience referred to hereinafter as PVOH, is produced by the hydrolysis of poly(vinyl acetate). PVOH is available commercially in several grades which differ in degree of polymerization and degree of hydrolysis. In general, the degree of polymerization will vary from about 500 to about 2,500; the corresponding molecular weights are from about 22,000 to about 110,000. The degree of hydrolysis usually will vary from about 85 percent to essentially 100 percent (e.g., 99.7 percent minimum hydrolysis). In addition, some modified PVOH materials also are available, such as so-called tackified grades which are borated PVOH resins (see U.S. Pat. No. 3,135,648).

Typical of the commercially available PVOH resins are the VINOL ® resins available from Air Products and Chemicals, Inc., Polymer Chemicals, Allentown, Pa. Preformed PVOH films also are commercially available, such as the MONO-SOL ® 1-000 series from Mono-Sol Division, Chris Craft Industries, Gary, Ind.

Preferably, the PVOH resin will have a relatively high degree of hydrolysis, typically essentially completely hydrolyzed, since such a resin does not require the use of a crosslinking agent.

Although resins having a lower degree of hydrolysis can be employed with satisfactory results, such resins may require the addition of a crosslinking agent in the aqueous solution of PVOH with which the porous substrate is coated, depending upon the requirements for the baffle, since such resins often are quite soluble in water at ambient temperature. However, inclusion of a crosslinking agent is not required, even for such resins.

Remarkably, such resins can be used to prepare satisfactory baffles. There are a number of porous substrates, meltblown webs in particular, which exhibit barrier properties with respect to menses. Such barrier properties, however, generally are insufficient to permit such porous substrates to serve by themselves as baffles having the requisite properties. Nevertheless, such substrates, when joined with a continuous film of a water-soluble polymeric material as described herein, yield baffles having properties which exceed the sum of the properties of the individual components making up the central zone of the baffle. That is, there is a kind of synergy which results from the combination of a porous substrate having significant barrier properties with a continuous film of a water-soluble polymeric material as described herein. For some applications, the porous substrate permits the use of polymeric materials which are quite soluble in water at ambient temperature, as already observed. As a practical matter, however, it is preferred that such continuous film is substantially insoluble in water having a temperature less than about 50 degrees C.

Suitable crosslinking agents for PVOH are those known in the art, such as glyoxal; formaldehyde; urea-formaldehydes; melamine-formaldehydes; metal compounds, such as cupric ammonium complexes, chromium complexes, organic titanates, and dichromates; and the like. When required, a crosslinking agent usually is employed in an amount in the range of from about 1 to about 5 percent by weight, based on the weight of PVOH in the aqueous solution, although higher or lower amounts can be employed if desired.

In addition to the use of chemical crosslinking agents as discussed above, the formed PVOH film can be crosslinked by radiation, such as electron beam radiation, ultraviolet radiation, and the like. The formed PVOH film also can be crosslinked thermally by heating the film to a temperature in excess of 100 degrees C. The preferred temperature range is from about 120 to about 180 degrees C. In the preferred temperature range, the heat-treatment time typically is about 1 hour. Thermal crosslinking is preferred over the inclusion of a chemical crosslinking agent in the coating solution.

Because flexibility of the breathable barrier often is a required characteristic, it may be either necessary or desirable to include a plasticizer in the PVOH coating solution. Suitable plasticizers in general are any of the known plasticizers for PVOH, such as glycerol, the poly(oxyethylene) diols, pentaerythritol, 1,2,6-hexanetriol, sorbitol, formamide, urea, and the like. Glycerol has been found to be a particularly useful plasticizer and is preferred. Thus, a plasticizer can be present in an amount of from 0 to about 50 percent by weight, based on the weight of PVOH employed, although somewhat higher amounts perhaps can be used, depending upon the polymeric material and its molecular weight range. When employed with PVOH resins, the plasticizer preferably will be present in an amount of from about 15 to about 25 percent by weight.

Some care must be exercised in the use of plasticizers, however. While plasticizers can increase film flexibility and enhance film formation, they also can adversely affect the menses barrier characteristics of the central zone, especially when used at unusually high levels. Thus, the plasticizer level in general should be kept to the minimum level which is consistent both with film formation and flexibility requirements and the desired properties of the baffle.

As indicated hereinbefore, the PVOH or other water-soluble polymeric material can be applied to the porous substrate as an aqueous solution. Application usually is made at ambient temperature and pressure, although such conditions are not mandatory. Indeed, any combination of temperature and pressure can be employed, although for reasons of economics and convenience, ambient temperature and pressure are preferred. The concentration of PVOH or other polymeric material in the solution is not known to be critical and usually is a matter of convenience. In practice, when the polymeric material is PVOH, concentrations of from about 4 to about 12 percent by weight are typical. The preferred concentration range is from about 5 to about 10 percent by weight as employed in the examples.

The method of application is not known to be critical and largely is a matter of convenience. Thus, the PVOH solution can be applied by spraying, dipping, brushing, doctor blade, roller, Meyer rod, and the like. In addition, a single coat or multiple coats can be applied. Moreover, if multiple coats are applied, the application solution does not have to be the same for each application. The several solutions can utilize different concentrations of the same PVOH resin, the presence or absence of such compounds as crosslinking agent and plasticizer, different PVOH resins at the same or different concentrations, or combinations of any of the foregoing variations.

After the aqueous solution of a poly(vinyl alcohol) has been applied to the porous substrate, the coated substrate is dried by removing water, preferably at an elevated temperature. The removal of water generally results in the formation of a film of the polymeric material. If a subsequent porous substrate is to be applied adjacent to the film, such application can be done before drying has been completed and is preferred. If desired, multiple coatings of the PVOH solution can be applied.

Finally, additives other than crosslinking agents and plasticizers can be incorporated into the PVOH aqueous coating solution or film, if desired. Such additives include binders, extenders, fillers, pigments dyes, defoamers, preservatives, fungicides, wetting agents, deodorants, fluorescent agents and the like.

Figure 2:
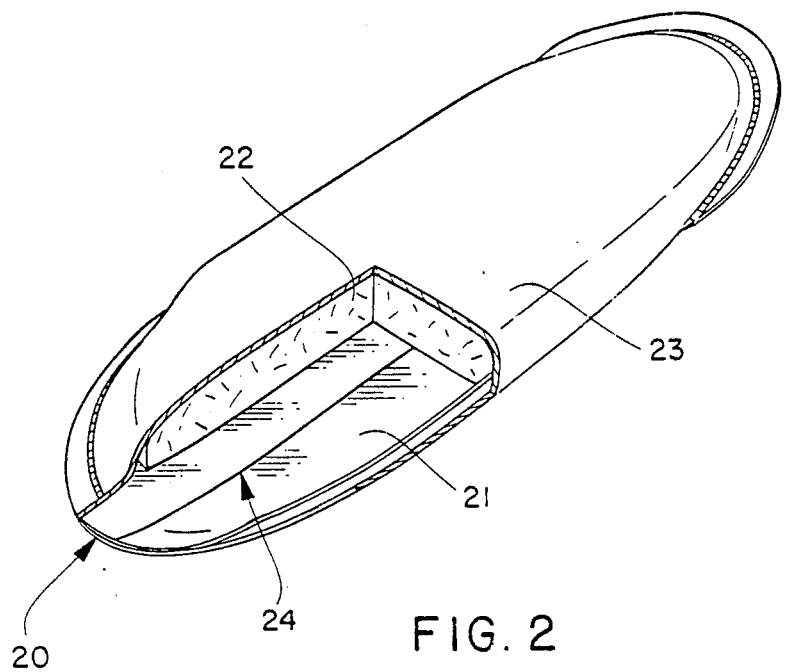

As already noted, the baffle of the present invention is especially well suited for use in a sanitary napkin or pad. Such use is illustrated by FIGS. 1 and 2. FIG. 1 is a perspective, cut away drawing of a sanitary pad having baffle of the present invention in which the central zone does not extend the length of the baffle. Thus, sanitary pad 10 comprises baffle 11 and absorbent material 12 wrapped with a fluid pervious cover 13. Baffle 11 has central zone 14. FIG. 2 differs from FIG. 1 only in the fact that the central zone extends the length of the baffle. Hence, sanitary pad 20 comprises baffle 21 and absorbent material 22 wrapped with a fluid pervious cover 23. The baffle 21 has central zone 24 extending the length of the baffle.

The present invention is further described by the examples which follow, illustrating preferred embodiment of the present invention. Such example is not to be construed as in any way limiting either the spirit or scope of the present invention.

In the examples, the water vapor transmission rate was determined in accordance with ASTM Method E 96-80, Standard Test Methods for Water Vapor Transmission of Materials, Procedure 12. The apparatus employed was a Vapometer (Catalog No. 68-1, Thwing-Albert Instrument Company, Philadelphia, Pa.). The apparatus consisted of a two-inch (about 5.1-cm) deep aluminum cup having a flanged top with a neoprene rubber gasket. The inner diameter of the flange was 2.5 inches (about 6.4 cm). About 100 ml of water was added to the cup and a sample of the sample to be tested was sealed mechanically over the open end of the cup and weighed. The sample-cup assembly was placed in an oven at 37 degrees C. and about 50 percent relative humidity. Periodic weighings of the sample-cup assembly permitted calculation of the water vapor transmission rate (WVTR).

The effectiveness of the baffle as a barrier to menses was measured by a static pressure test. The sample to be tested, which usually was either baffle material or central zone material, was placed over a 3-inch by 5-inch piece of blotter paper. The sample to be tested was placed over the blotter paper, the outermost surface adjacent to the blotter paper, i.e., body side up. The sample then was covered by fluff from a standard sanitary pad. The fluff pad weighed about 10 g and was about 21 cm long and about 6 cm wide. Fifteen ml of a synthetic menses was added to the center of the fluff in a precisely controlled rectangular area having an approximate major axis:minor axis ratio of 10:1. The synthetic menses was glycerin based and had a viscosity of 16.3 cps at 20 degrees C. and a surface tension of 51.6 dynes/cm at 20 degrees C. A weight then was placed on top of the fluff for a specified period of time. The blotter paper was inspected periodically for wetness. Weights were conveniently provided by placing bird shot in suitable containers, typically in one-quarter pound increments. The weights were adjusted so that the pressure on the wetted fluff took into account the area of the container which in turn was sized to properly accommodate the wetted area. That is, the pressure applied to the wetted fluff was equal to the total weight of the container divided by the area of contact, i.e., the area of the bottom of the container.

EXAMPLE 1

An approximately five percent by weight aqueous solution of a poly(vinyl alcohol) was prepared by dispersing the resin in water at ambient temperature and heating the mixture at about 96 degrees C. with moderate agitation until the resin dissolved. The poly(vinyl alcohol) employed was VINOL ® 125 (Air Products and Chemicals, Inc., Polymer Chemicals, Allentown, Pa.). According to information supplied by the manufacturer, the resin was in excess of 99.3 percent hydrolyzed and a 4 percent by weight aqueous solution of the resin at 20 degrees C. had a viscosity of 26–30 cps. The resulting solution then was allowed to cool to ambient temperature.

The above PVOH solution then was applied by means of a brush in a 3.8-cm wide strip on a baffle material which consisted of a meltblown-bonded carded web laminate; the laminate was prepared by forming the meltblown web directly onto the bonded carded web. The resin solution was applied to the meltblown side of the laminate. The coated material was air dried at ambient temperature overnight. The meltblown web had a nominal basis weight of 25 g/m$^2$, the bonded carded web had a nominal basis weight of 18 g/m$^2$, and the level of PVOH add-on was 4.5 g/m$^2$.

The coated area or central zone was too narrow to measure the water vapor transmission rate of the coated portion. However, the central zone did not leak under the static pressure test at the highest pressure employed, which was 1.5 psi. Ten samples of the uncoated portion of the baffle material were tested at the same pressure; one leak was observed.

Because the water vapor transmission rate of the coated area or central zone of Example 1 could not be measured, various nonwoven webs were coated as described in Example 1 and the water vapor transmission rates of the resulting composites measured and compared with those of the uncoated webs. These comparisons are described in the examples which follow.

EXAMPLE 2

The procedure of Example 1 was repeated, except that the poly(vinyl alcohol) resin was VINOL® 165 (Air Products and Chemicals, Inc., Polymer Chemicals, Allentown, Pa.) and the nonwoven web was a polypropylene meltblown web having a nominal basis weight of 34 g/m$^2$. According to information supplied by the manufacturer, the resin was in excess of 99.3 percent hydrolyzed and a 4 percent by weight aqueous solution of the resin at 20 degrees C. had a viscosity of 55–65 cps. The coated sample was air dried overnight at ambient temperature. The PVOH add-on was 17 g/m$^2$. The coated sample gave a water vapor transmission rate of 1171 g/m$^2$/24 hours, whereas an uncoated sample gave a water vapor transmission rate of 2518 g/m$^2$/24 hours.

EXAMPLE 3

The procedure of Example 1 was repeated, except that the coating solution was an eight percent by weight solution of VINOL® 125 in water, the nonwoven web was a polypropylene meltblown web having a nominal basis weight of 25 g/m$^2$, and the coating solution was applied by means of a No. 22 Meyer rod. The coated sample was dried at about 140 degrees C. for two minutes. The PVOH add-on was 5.3 g/m$^2$. The water vapor transmission rate of the coated sample was 1761 g/m$^2$/24 hours and the water vapor transmission rate of the uncoated sample was 3111 g/m$^2$/24 hours.

EXAMPLE 4

The procedure of Example 3 was repeated, except that a second coating of the PVOH solution was applied over the first coating after the sample had been dried; the total PVOH add-on was 7.1 g/m$^2$. The double-coated sample gave a water vapor transmission rate of 1348 g/m$^2$/24 hours.

EXAMPLE 5

The procedure of Example 3 was repeated, except that the PVOH solution was replaced with a ten percent by weight solution of VINOL® SH-72 (Air Products and Chemicals, Inc., Polymer Chemicals, Allentown, Pa.). According to information supplied by the manufacturer, the resin was a tackified (borated) grade derived from VINOL® 165. The viscosity of a ten percent by weight aqueous solution of the resin at 25 degrees C. was reported to be 3800–5500 cps. The PVOH add-on was 7.7 g/m$^2$. The coated sample gave a water vapor transmission rate of 1714 g/m$^2$/24 hours.

EXAMPLE 6

The procedure of Example 3 was repeated, except that the PVOH solution also contained 1 percent by weight glycerol, or about 12 percent by weight, based on the weight of PVOH. The add-on of the PVOH composition was 5.3 g/m$^2$. The coated sample gave a water vapor transmission rate of 2392 g/m$^2$/24 hours.

Having thus described the invention, numerous changes and modifications thereof will be readily apparent to those having ordinary skill in the art without departing from the spirit or scope of the invention.

What is claimed is:

1. A baffle having a central zone extending along at least a portion of the length thereof,
    A. said zone being impermeable to menses under a static pressure of from about 1 to about 3 psi for a period of at least about one hour and having a water vapor transmission rate at 37 degrees C. and about 50 percent relative humidity of from about 50 to about 2,500 g/m$^2$/24 hours,
    B. with the non-central zone portions of the baffle being impermeable to menses under a static pressure of from about 0.1 to about 1 psi for a period of at least about one hour and having a water vapor transmission rate at 37 degrees C. and about 50 percent relative humidity of from about 1,500 to about 5,000 g/m$^2$/24 hours;
in which said baffle comprises a fibrous porous substrate and a water vapor-permeable material overlaying and joined to said fibrous porous substrate in the area of said central zone; with the proviso that the water vapor transmission rate of the central zone is less than that of the non-central zone portions of the baffle.

2. The baffle of claim 1, in which said zone is impermeable to menses under a static pressure of from about 1.5 to about 2.5 psi.

3. The baffle of claim 1, in which said zone has a water vapor transmission rate of from about 500 to about 1,500 g/m$^2$/24 hours.

4. The baffle of claim 1, in which said non-central zone is impermeable to menses under at static pressure of from about 0.5 to about 0.75 psi.

5. The baffle of claim 1, in which said non-central zone has a water vapor transmission rate of from about 1,500 to about 3,500 g/m$^2$/24 hours.

6. The baffle of claim 1, in which said central zone extends along the entire length thereof.

7. The baffle of claim 1, in which the length of said central zone is at least about one-third that of the baffle.

8. The baffle of claim 7, in which said central zone is located approximately equidistant from the ends of the baffle.

9. The baffle of claim 1, in which said fibrous porous substrate is a nonwoven web.

10. The baffle of claim 9, in which said nonwoven web is a meltblown web.

11. The baffle of claim 10, in which said meltblown web is comprised of polyolefin fibers.

12. The baffle of claim 11, in which said polyolefin fibers are polypropylene fibers.

13. The baffle of claim 1, in which said water vapor-permeable material is a water-soluble polymeric material.

14. The baffle of claim 13, in which said water-soluble polymeric material is a continuous film of a poly(vinyl alcohol), which film:
   A. is not microporous in that it is substantially free of voids which connect the two surfaces of the film; and
   B. has an average thickness of from about 3 to about 250 microns.

15. The baffle of claim 14, in which said film is substantially insoluble in water having a temperature less than about 50 degrees C.

16. The baffle of claim 14, in which the side of the film overlaying and joined to said fibrous porous substrate is intimately comingled with at least some of the fibers of the continuous film side of said fibrous porous substrate and none of the pores of the surface of said fibrous porous substrate joined to said continuous film are so large as to significantly adversely affect the barrier properties of said baffle as a consequence of said comingling.

17. The baffle of claim 9, in which said water vapor-permeable material is a continuous film of a poly(vinyl alcohol), which film:
   A. is not microporous in that it is substantially free of voids which connect the two surfaces of the film; and
   B. has an average thickness of from about 3 to about 250 microns;
wherein the side the film overlaying and joined to said nonwoven web is intimately comingled with at least some of the fibers of the continuous film side of said nonwoven web and none of the pores of the surface of said nonwoven web joined to said continuous film are so large as to significantly adversely affect the barrier properties of said baffle as a consequence of said comingling.

18. The baffle of claim 17, in which said film is substantially insoluble in water having a temperature less than about 50 degrees C.

19. The baffle of claim 10, in which said water vapor-permeable material is a continuous film of a poly(vinyl alcohol), which film:
   A. is not microporous in that it is substantially free of voids which connect the two surface of the film; and
   B. has an average thickness of from about 3 to about 250 microns;
wherein the side of the film overlaying and joined to said meltblown web is intimately comingled with at least some of the fibers of the continuous film side of said meltblown web and none of the pores of the surface of said meltblown web joined to said continuous film are so large as to significantly adversely affect the barrier properties of said baffle as a consequence of said comingling.

20. The baffle of claim 19, in which said film is substantially insoluble in water having a temperature less than about 50 degrees C.

21. The baffle of claim 19, in which each of at least about 50 percent of the pores at the surface of the meltblown web to which said film is joined has a cross-sectional area of less than about $3.2 \times 10^{-8}$ m$^2$.

22. The baffle of claim 21, in which essentially none of the pores at the surface of the meltblown web has a cross-sectional area in excess of about $3.2 \times 10^{-8}$ m$^2$.

23. The baffle of claim 11, in which said water vapor-permeable material is a continuous film of a poly(vinyl alcohol), which film;
   A. is not microporous in that it is substantially free of voids which connect the two surfaces of the film; and
   B. has an average thickness of from about 3 to about 250 microns;
wherein the side of the film overlaying and joined to said meltblown web is intimately comingled with at least some of the fibers of the continuous film side of said meltblown web and none of the pores of the surface of said meltblown web joined to said continuous film are so large as to significantly adversely affect the barrier properties of said baffle as a consequence of said comingling.

24. The baffle of claim 23, in which said film is substantially insoluble in water having a temperature less than about 50 degrees C.

25. The baffle of claim 23, in which each of at least about 50 percent of the pores at the surface of the meltblown web to which said film is joined has a cross-sectional area of less than about $3.2 \times 10^{-8}$ m$^2$.

26. The baffle of claim 25, in which essentially none of the pores at the surface of the meltblown web has a cross-sectional area in excess of about $3.2 \times 10^{-8}$ m$^2$.

27. The baffle of claim 12, in which said water vapor-permeable material is a continuous film of a poly(vinyl alcohol), which film:
   A. is not microporous in that it is substantially free of voids which connect the two surfaces of the film; and
   B. has an average thickness of from about 3 to about 250 microns;
wherein the side of the film overlaying and joined to said meltblown web is intimately comingled with at least some of the fibers of the continuous film side of said meltblown web and none of the pores of the surface of said meltblown web joined to said continuous film are so large as to significantly adversely affect the barrier properties of said baffle as a consequence of said comingling.

28. The baffle of claim 27, in which said film is substantially insoluble in water having a temperature less than about 50 degrees C.

29. The baffle of claim 27, in which each of at least about 50 percent of the pores at the surface of the meltblown web to which said film is joined has a cross-sectional area of less than about $3.2 \times 10^{-8}$ m$^2$.

30. The baffle of claim 29, in which essentially none of the pores at the surface of the meltblown web has a cross-sectional area in excess of about $3.2 \times 10^{-8}$ m$^2$.

31. A sanitary napkin comprising an absorbent batt, a fluid-permeable cover, and the baffle of claim 1.

32. A sanitary napkin comprising an absorbent batt, a fluid-permeable cover, and the baffle of claim 2.

33. A sanitary napkin comprising an absorbent batt, a fluid-permeable cover, and the baffle of claim 3.

34. A sanitary napkin comprising an absorbent batt, a fluid-permeable cover, and the baffle of claim 4.

35. A sanitary napkin comprising an absorbent batt, a fluid-permeable cover, and the baffle of claim 5.

36. A sanitary napkin comprising an absorbent batt, a fluid-permeable cover, and the baffle of claim 6.

37. A sanitary napkin comprising an absorbent batt, a fluid-permeable cover, and the baffle of claim 7.

38. A sanitary napkin comprising an absorbent batt, a fluid-permeable cover, and the baffle of claim 8.

39. A sanitary napkin comprising an absorbent batt, a fluid-permeable cover, and the baffle of claim 14.

40. A sanitary napkin comprising an absorbent batt, a fluid-permeable cover, and the baffle of claim 16.

41. A sanitary napkin comprising an absorbent batt, a fluid-permeable cover, and the baffle of claim 17.

42. A sanitary napkin comprising an absorbent batt, a fluid-permeable cover, and the baffle of claim 19.

43. A sanitary napkin comprising an absorbent batt, a fluid-permeable cover, and the baffle of claim 23.

44. A sanitary napkin comprising an absorbent batt, a fluid-permeable cover, and the baffle of claim 27.

* * * * *